United States Patent [19]

Osborne

[11] Patent Number: 4,634,433
[45] Date of Patent: Jan. 6, 1987

[54] FLEXIBLE SHEATH ASSEMBLY FOR AN INDWELLING CATHETER

[75] Inventor: Thomas A. Osborne, Bloomington, Ind.

[73] Assignee: Cook, Incorporated, Bloomington, Ind.

[21] Appl. No.: 731,138

[22] Filed: May 6, 1985

Related U.S. Application Data

[63] Continuation of Ser. No. 433,256, Oct. 7, 1982, Pat. No. 4,551,137.

[51] Int. Cl.⁴ .......................................... A61M 25/00
[52] U.S. Cl. ..................................... 604/171; 604/163
[58] Field of Search ............... 604/171, 172, 163, 164; 206/802, 364, 365

[56] References Cited

U.S. PATENT DOCUMENTS

| | | | |
|---|---|---|---|
| 3,528,825 | 9/1970 | Doughty | 206/802 X |
| 3,894,540 | 7/1975 | Bonner | 604/171 |
| 4,104,774 | 8/1978 | Overmeyer et al. | 206/802 |
| 4,241,828 | 12/1980 | Bourdelle et al. | 206/802 X |
| 4,327,723 | 5/1982 | Frankhouser | 604/171 |

Primary Examiner—Stephen C. Pellegrino
Attorney, Agent, or Firm—Woodard, Weikart, Emhardt & Naughton

[57] ABSTRACT

A flexible sheath assembly for an indwelling catheter is provided which maintains the sterility of an otherwise exposed portion of an indwelling catheter so that the depth of insertion of the catheter within a body may be adjusted without causing contamination. The assembly includes a transparent flexible sheathing which is sealingly secured at its ends to front and rear hubs each having a passageway therethrough which is sized to permit passage of a catheter. The flexible sheathing is longitudinally expandable from a collapsed position wherein the sheathing is twisted about an axis substantially parallel to the length of the sheath. The flexible sheathing in the collapsed position defines a central passageway which is aligned with the front and rear hub passageways for permitting the catheter to be guided through the interior of the flexible sheathing as it is passed between the front and rear hubs. The central passageway is heat set in the flexible sheathing by placing the flexible sheath on a mandrel in its contracted position and heating the flexible sheath in an oven.

2 Claims, 4 Drawing Figures

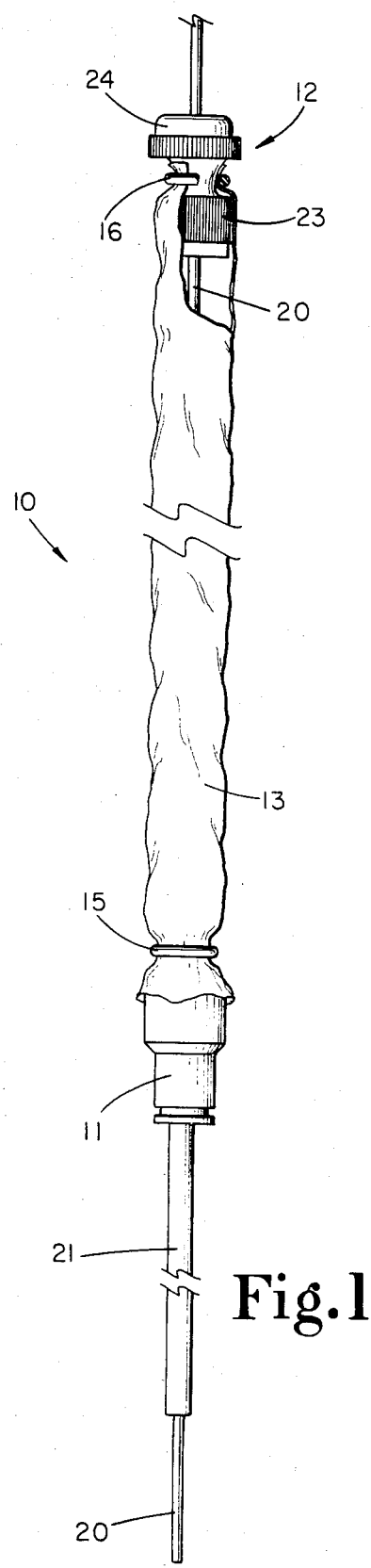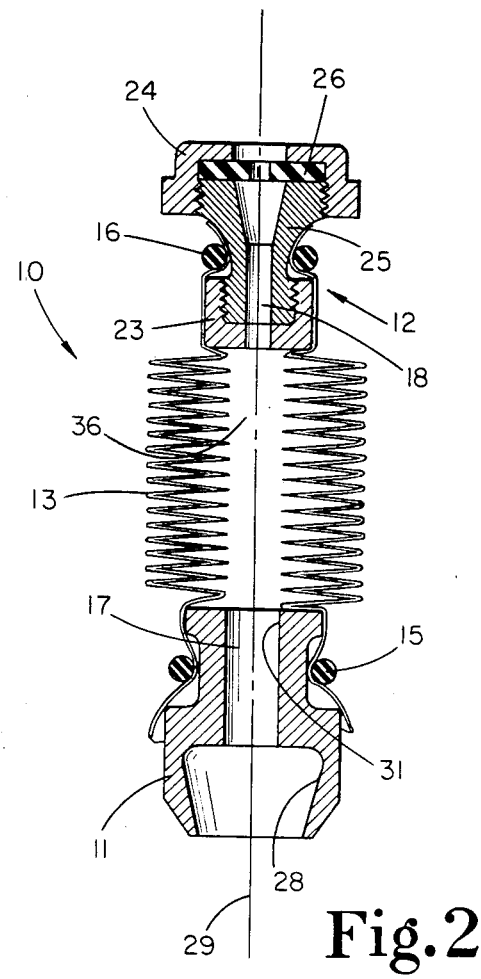

FLEXIBLE SHEATH ASSEMBLY FOR AN INDWELLING CATHETER

This application is a continuation of application Ser. No. 433,256, filed 10/7/82 now U.S. Pat. No. 4,551,137.

BACKGROUND OF THE INVENTION

1. Field of the Invention

The present invention is related generally to the field of sterility devices for catheters and, more specifically, to flexible sheath devices for protecting the sterility of the exposed portions of indwelling catheters.

2. Description of the Prior Art

It is frequently desirable to adjust the depth of insertion of an indwelling catheter which has already been left indwelling for an extended period of time. One example of such a situation occurs when a balloon-tipped catheter inserted within the heart to measure certain heart activities becomes somehow later dislodged. This may necessitate further insertion of the catheter in order to properly relocate the heart activity sensor. In such situations it is of utmost importance that the sterility of the exposed catheter portion be maintained.

The problem of protecting the sterility of exposed portions of an indwelling catheter has been long and well known in the medical art. Thus, prior art includes several patented devices which protect sterility of the exposed portion of an indwelling catheter. An early example, U.S. Pat. No. 3,867,937 to Schwartz, discloses a protective sheath comprising a very thin plastic tubular member which is in a loose sliding fit on the outer diameter of the catheter forward of the rear hub end thereof. The protective sheath collapses as the catheter is inserted to a desired body depth, with the forward end of the sheath contacting the skin adjacent the entrance site. While this device offers the advantages of a very simple construction, it lacks an airtight seal at the forward end of the sheath. Thus, this device inherently does not prevent the catheter portion residing within the sheath from becoming contaminated by outside bacteria entering through the unsealed area between the catheter and the forward end of the sheath or from bacteria which may be present at the skin entrance site.

Two very recent patent references disclose catheter sheath devices which are intended to provide a totally enclosed or sealed environment along a length of the exposed portion of an indwelling catheter, thus permitting later adjustment of the depth of insertion without creating an unacceptable risk of infection. U.S. Pat. No. 4,327,723 to Frankenhouser discloses a shield assembly including front and rear hubs sized to permit movement of the catheter therethrough, a feed tube for connecting the front and rear hubs, and a flexible sheath connecting the front and rear hubs. The front hub is connected to the rear portion of a hollow introducer which serves to facilitate the introduction of the catheter into the body. With this device, a relatively long and rigid inner feed tube is necessary to guide the catheter through the flexible sheath portion of the assembly. The feed tube serves no further use once the catheter is introduced into the body. U.S. Pat. No. 4,327,735 to Hampson discloses a device similar to the flexible sheath assembly disclosed by Frankenhouser except that the feed tube is adapted to be removed from the assembly once it has served the purpose of guiding the catheter through the interior of the flexible sheath.

The present invention discloses a flexible sheath assembly which affords all of the advantages of a totally sealed catheter sheath assembly, as disclosed in the Frankenhouser and Hampson references, but further having a more simplified construction which eliminates the need for a relatively rigid feed tube within the flexible sheath.

Other references which may have some relevance are:

| Patent No. | Inventor |
| --- | --- |
| 4,250,881 | Smith |
| 4,235,232 | Spaven et al. |
| 4,160,450 | Doherty |
| 4,079,738 | Dunn |
| 4,037,600 | Poncy |
| 3,991,762 | Radford |
| 3,894,540 | Bonner |
| 3,825,001 | Bennet |
| 3,709,223 | Macalalad et al. |
| 3,474,786 | Spademan |
| 3,335,723 | Waldman |
| 3,185,151 | Czorny |
| 3,010,453 | Doherty |
| 2,937,643 | Elliot |
| 4,062,363 | Bonner |
| 4,029,099 | Fifield |
| 3,902,500 | Dryden |
| 3,648,704 | Jackson |
| 3,792,703 | Moorhead |
| 3,854,483 | Powers |
| 3,898,993 | Taniguchi |
| 4,006,743 | Kowarski |
| 4,000,739 | Stevens |

Accordingly, it is an object of the present invention to provide an improved flexible catheter sheath assembly for an indwelling catheter.

This and other objects of and advantages of the present invention will become more apparent in the following figures and detailed description.

SUMMARY OF THE INVENTION

One embodiment of the present invention is characterized by a flexible sheath assembly for an indwelling catheter. The assembly includes a front and a rear hub each having a passageway therethrough which is sized to permit passage of the catheter. The assembly further includes a flexible sheathing which is sealingly secured to the front and rear hubs. The flexible sheathing is capable of being longitudinally expanded from a collapsed position wherein the flexible sheathing is twisted about an axis substantially parallel to the direction of longitudinal expansion of the flexible sheathing. In the collapsed position the flexible sheathing defines a central passageway aligned with the front and rear hub passageways for receiving the catheter therethrough. In the longitudinally expanded position the flexible sheath assembly maintains the sterility of an otherwise exposed portion of the catheter, thereby permitting the depth of catheter insertion within the body to be adjusted after the catheter has been left indwelling for extended periods.

BRIEF DESCRIPTION OF THE DRAWINGS

FIG. 1 is a side elevation view partially in section showing the flexible sheath assembly of the present invention in its longitudinally expanded position disposed over a catheter and attached to a catheter introducer.

FIG. 2 is a longitudinal sectional view showing the flexible sheath assembly of the present invention in its collapsed position.

DESCRIPTION OF THE PREFERRED EMBODIMENT

Figure 3:
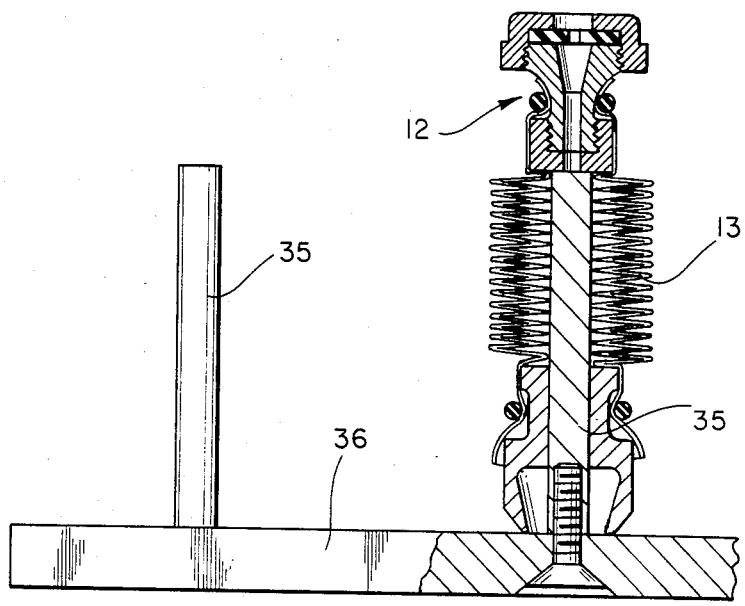
FIG. 3 is a side elevation of a curing fixture for manufacture of the sleeve.
Figure 4:
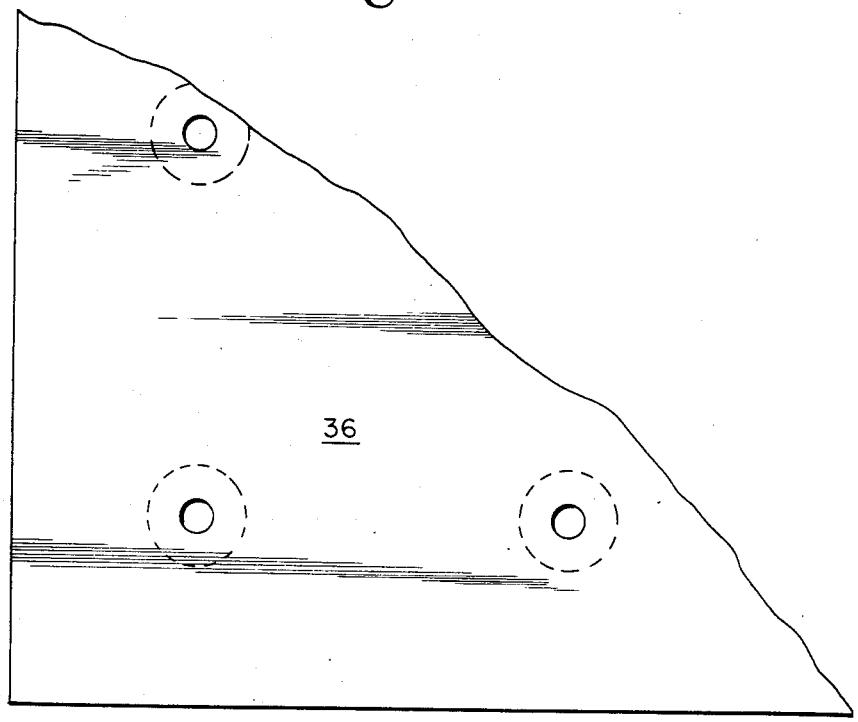
FIG. 4 is a fragmentary top plan view of the curing fixture of FIG. 3.

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings, the flexible sheath assembly of the present invention is generally designated at 10. Sheath assembly 10 includes front hub 11 and rear hub assembly 12 which are interconnected by a transparent flexible sheathing 13. Flexible sheathing 13 extends between front hub 11 and rear hub assembly 12 and is sealingly secured thereto by O-rings 15 and 16, respectively. Front hub 11 and rear hub assembly 12 have respective passageways 17 and 18 therethrough which permit the passage of catheter 20. Catheter 20 and introducer 21 are of conventional construction and those skilled in the art will readily recognize that no further description thereof is necessary.

Front hub 11 includes a socket portion 28 which is coupled over the distal end of introducer 21. Front hub 11 is made from a deformable plastic or rubber material which permits front hub 11 to be sealingly coupled with introducer 21. Rear hub assembly 12 includes hub 23 and cap 24 which are interconnected by coupling member 25, which is externally threaded at both ends for coupling with the internally threaded portions of hub 23 and 24. A gasket 26 is fitted between cap 24 and coupling member 25 and extends partially within passageway 18 thereby serving to seal the space between rear hub assembly 12 and catheter 20 while permitting catheter 20 to be freely passed through rear hub assembly 12. While gasket 26 may be made of any suitable material, it has been found that a silicone rubber gasket is acceptable for this purpose.

It should be noted that the construction of rear hub assembly 12 may be considerably varied without departing from the scope and spirit of the invention. For example, hub 23, cap 24 and coupling member 25 may alternatively be one integrally formed part, it being understood that means be provided in rear hub assembly 12 for sealing the space between it and catheter 20 while allowing catheter 20 to be passed easily through rear hub assembly 12.

It is to be understood that sheath assembly 10 is in its collapsed position as depicted in FIG. 2 until such time as catheter 20 has been successfully passed through the sheath assembly. In the collapsed position sheathing 13 of sheath assembly 10 is completely contracted along axis 29 into a series of tightly packed and twisted folds. Sheath assembly 10 is preferably provided to the physician in its collapsed position prepackaged in a kit with catheter 20 and introducer 21. In order for sheath assembly 10 to maintain its collapsed position so that catheter 20 may be easily and quickly passed therethrough to perform a catheterization, the flexible sheathing 13 is packed tightly and twisted on and about the axis of a mandrel 35 upon which the sheath assembly 10 is received through front hub 11. The entire sheath assembly 10, mandrel and fixture 36 is then placed inside an oven and heated for the purpose of causing the flexible sheathing to take a set. In one preferred embodiment of the invention the flexible sheathing 13 was made of 0.003 inch thickness polyethylene plastic sleeving. Such flexible sheathing 13 properly sets after being baked for a period of approximately 45 minutes at a temperature of approximately 190 degrees F. After such baking the curing fixture 36 is removed from the oven and allowed to cool to room temperature for 15 minutes before removing the sterility sleeve from the mandrel.

It is to be noted that even though this process causes sheath assembly 10 to maintain its collapsed position prior to use, the flexible sheathing 13 can later be easily longitudinally expanded so as to shield an otherwise exposed length of catheter 20. When thus formed, the tightly packed and and twisted folds of flexible sheathing 13 define a central passageway 36 which is in the shape of the external surface of the mandrel and aligned with hub passageways 17 and 18. Preferably, this central passageway will be cylindrically shaped with a diameter slightly larger than that of catheter 20, but smaller than the corresponding diameter of passageway 17 at the interior end 31 thereof. The set in the flexible sheathing 13 in the collapsed portion resiliently maintains the size, shape and straightness of the central passageway 36. This permits catheter 20 to be easily guided through sheathing 13 to within passageway 17 of front hub 11, thus ensuring easy passage of catheter 20 through the entire sheath assembly 10.

It may thus be readily appreciated that the present invention discloses a catheter assembly which completely seals an otherwise exposed portion of an indwelling catheter. The invention has the advantages of a simple construction and method of manufacture thus offering cost savings while also making the assembly simple to use.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

I claim:

1. A flexible sheath for shielding a catheter disposed therethrough, comprising:
   front and rear hubs each having a passageway therethrough sized to permit movement therethrough of said catheter;
   tubular flexible sheathing having two ends with one end sealingly connected to said front hub and the other end sealingly connected to said rear hub;
   said flexible sheathing including means for maintaining said flexible sheathing in an initial contracted orientation wherein said hubs are relatively close together and said sheathing defines a central passageway aligned with said hub passageways, said central passageway being sized to permit movement therethrough of said catheter;

said flexible sheathing being capable of being expanded from said contracted orientation to an expanded orientation wherein said flexible sheathing shields a greater length of said catheter than is shielded when said flexible sheathing is in said contracted orientation.

2. A flexible sheath for shielding a catheter disposed therethrough, comprising:

front and rear hubs each having a passageway therethrough sized to permit movement therethrough of said catheter;

tubular flexible sheathing having two ends with one end sealingly connected to said front hub and the other end sealingly connected to said rear hub, said flexible sheathing having a rigidifying set biasing it in an initial contracted orientation wherein said hubs are relatively close together, said flexible sheathing defining a central passageway aligned with said hub passageways, said central passageway being sized to permit movement therethrough of said catheter;

said flexible sheathing being capable of being expanded from said contracted orientation to an expanded orientation wherein said flexible sheathing shields a greater length of said catheter than is shielded when said flexible sheathing is in said contracted orientation.

* * * * *